United States Patent
Yoon

(12)
(10) Patent No.: US 6,277,089 B1
(45) Date of Patent: Aug. 21, 2001

(54) METHOD FOR ABLATING PORTIONS OF THE UTERUS

(76) Inventor: InBae Yoon, 11886 Farside Rd., Ellicott City, MD (US) 21042

(*) Notice: Subject to any disclaimer, the term of this patent is extended or adjusted under 35 U.S.C. 154(b) by 0 days.

(21) Appl. No.: 09/052,134

(22) Filed: Mar. 31, 1998

Related U.S. Application Data

(63) Continuation of application No. 08/595,461, filed on Feb. 5, 1996, now Pat. No. 5,773,252, and a continuation-in-part of application No. 08/768,239, filed on Dec. 17, 1996, now Pat. No. 5,782,800, which is a continuation of application No. 08/441,465, filed on May 15, 1995, now Pat. No. 5,656,013, which is a continuation of application No. 08/295,022, filed on Aug. 25, 1994, now abandoned, which is a division of application No. 08/249,116, filed on May 25, 1994, now Pat. No. 5,514,091, which is a division of application No. 08/130,484, filed on Oct. 1, 1993, now Pat. No. 5,484,426, which is a division of application No. 07/600,775, filed on Oct. 23, 1990, now Pat. No. 5,374,261, which is a continuation-in-part of application No. 07/556,081, filed on Jul. 24, 1990, now Pat. No. 5,074,840, which is a continuation-in-part of application No. 07/596,937, filed on Oct. 15, 1990, now abandoned.

(51) Int. Cl.[7] .......................... A61M 35/00; A61B 18/04; A61B 18/18

(52) U.S. Cl. .................... 604/1; 606/32; 606/40; 606/49; 606/190

(58) Field of Search ........................ 604/1–3, 11; 606/32, 606/37, 40, 49, 190; 600/101, 104

(56) References Cited

U.S. PATENT DOCUMENTS

| | | | |
|---|---|---|---|
| 0,654,564 | 7/1900 | Dargatz | 604/13 |
| 0,682,090 | 9/1901 | Lee . | |
| 0,702,997 | 6/1902 | Pugh | 604/13 |

(List continued on next page.)

FOREIGN PATENT DOCUMENTS

| | | |
|---|---|---|
| 1123155 | 5/1982 | (CA) . |
| 3519626 | 12/1986 | (DE) . |
| 0278937 | 8/1988 | (EP) . |
| 0432363 | 6/1991 | (EP) . |
| 2139898 | 11/1984 | (GB) . |

OTHER PUBLICATIONS

Expose Retractor: Inflatable Retractor, Advanced Surgical, Product Specification sheet.

Delivering the Future First . . . , Origin, Product Specification Sheet 1994.

(List continued on next page.)

*Primary Examiner*—Dennis Ruhl
(74) *Attorney, Agent, or Firm*—Blank Rome Comisky & McCauley LLP

(57) ABSTRACT

A multifunctional device for use in an endoscopically performed operative procedure of the type where a narrow portal is established through the skin to provide access to an operative site and the multifunctional device is introduced to the operative site through the narrow portal. The multifunctional device is formed of an absorbent material, preferably expandable, having a substantially rigid dry state prior to introduction to the operative site and a soft, flexible wet state after absorbing fluids. The absorbent material can be formed with a spine therein of either a continuous or a discontinuous, segmented construction, and the spine can be branched and tubular or solid. The absorbent material can have portions or segments thereof expandable to different sizes to produce rounded protuberances to facilitate manipulation at the operative site and can have predetermined, non-straight configurations in the wet state, the predetermined configurations being controlled by the spine in the absorbent material or the method of forming the absorbent material. The multifunctional device can have a passage therethrough to accommodate laser, electrosurgical, biopsy or culturing instruments.

25 Claims, 3 Drawing Sheets

U.S. PATENT DOCUMENTS

| | | | |
|---|---|---|---|
| 0,716,040 | 12/1902 | Holt | 604/15 |
| 1,523,943 | 1/1925 | Fowle | 604/1 |
| 1,562,656 | 11/1925 | Park . | |
| 1,909,967 | 5/1933 | Jones . | |
| 2,524,195 | 10/1950 | Hoover | 128/260 |
| 3,039,468 | 6/1962 | Price | 128/347 |
| 3,095,877 | 7/1963 | Rowan | 128/260 |
| 3,253,594 | 5/1966 | Matthews | 128/348 |
| 3,459,175 | 8/1969 | Miller | 128/2 |
| 3,495,586 | 2/1970 | Regenbogen | 128/6 |
| 3,512,528 | 5/1970 | Whitehead | 128/285 |
| 3,557,794 | 1/1971 | Van Patten | 128/345 |
| 3,598,119 | 8/1971 | White | 128/215 |
| 3,635,223 | 1/1972 | Klieman | 128/348 |
| 3,683,915 | 8/1972 | Voss | 128/285 |
| 3,790,433 | 2/1974 | Baron | 161/113 |
| 3,799,173 | 3/1974 | Kamen | 128/351 |
| 3,833,003 | 9/1974 | Tarricco | 128/347 |
| 3,882,852 | 5/1975 | Sinnreich | 128/4 |
| 3,890,970 | 6/1975 | Gullen | 128/215 |
| 3,941,125 | 3/1976 | Drake | 128/155 |
| 3,952,742 | 4/1976 | Taylor | 128/172.1 |
| 4,019,499 | 4/1977 | Fitzgerald | 128/1 R |
| 4,027,673 | 6/1977 | Poncy | 128/285 |
| 4,043,338 | 8/1977 | Homm | 128/260 |
| 4,077,412 | 3/1978 | Moossun | 128/347 |
| 4,089,337 | 5/1978 | Kronner | 128/348 |
| 4,192,300 | 3/1980 | Devers | 128/155 |
| 4,219,026 | 8/1980 | Layton | 128/325 |
| 4,291,687 | 9/1981 | Sinnreich | 128/129 |
| 4,328,804 | 5/1982 | Shimatani | 128/285 |
| 4,329,990 | 5/1982 | Sneider | 128/239 |
| 4,335,720 | 6/1982 | Glassman | 128/270 |
| 4,372,295 | 2/1983 | Heckele | 128/4 |
| 4,421,504 | 12/1983 | Kline | 604/12 |
| 4,430,076 | 2/1984 | Harris | 604/96 |
| 4,535,773 | 8/1985 | Yoon | 604/51 |
| 4,553,965 | 11/1985 | Conn | 604/286 |
| 4,573,964 | 3/1986 | Huffman | 604/15 |
| 4,575,371 | 3/1986 | Nordqvist | 604/96 |
| 4,607,619 | 8/1986 | Seike | 128/4 |
| 4,608,965 | 9/1986 | Anspach, Jr. | 128/4 |
| 4,610,659 | 9/1986 | Friese | 604/11 |
| 4,748,982 | 6/1988 | Horzewski | 128/344 |
| 4,775,362 | 10/1988 | Kronner | 604/96 |
| 4,822,332 | 4/1989 | Kajander | 604/16 |
| 4,857,044 | 8/1989 | Lennon | 604/14 |
| 4,895,559 | 1/1990 | Shippert | 604/15 |
| 4,900,315 | 2/1990 | Lundqvist et al. | 604/311 |
| 4,950,280 | 8/1990 | Brennan | 606/196 |
| 4,966,583 | 10/1990 | Debbas | 604/98 |
| 5,002,557 | 3/1991 | Hasson | 606/191 |
| 5,002,558 | 3/1991 | Klein | 606/192 |
| 5,007,895 | 4/1991 | Burnett | 604/11 |
| 5,007,898 | 4/1991 | Rosenbluth | 604/54 |
| 5,009,639 | 4/1991 | Keymling | 604/96 |
| 5,030,227 | 7/1991 | Rosenbluth | 606/192 |
| 5,041,093 | 8/1991 | Chu | 604/104 |
| 5,045,056 | * 9/1991 | Behl | 604/49 |
| 5,074,840 | 12/1991 | Yoon | 604/15 |
| 5,074,871 | 12/1991 | Groshong | 606/170 |
| 5,084,044 | * 1/1992 | Quint | 606/27 |
| 5,103,804 | 4/1992 | Abele | 128/4 |
| 5,113,846 | 5/1992 | Hiltebrandt | 128/20 |
| 5,120,301 | 6/1992 | Wu | 604/3 |
| 5,122,137 | * 6/1992 | Lennox | 606/40 |
| 5,163,949 | 11/1992 | Bonutti | 606/192 |
| 5,176,128 | 1/1993 | Andrese | 128/20 |
| 5,178,133 | 1/1993 | Pena | 128/20 |
| 5,183,464 | 2/1993 | Dubrul | 128/3 |
| 5,188,630 | 2/1993 | Christoudias | 606/1 |
| 5,195,507 | 3/1993 | Bilweis | 128/20 |
| 5,197,948 | 3/1993 | Ghodsian | 604/30 |
| 5,197,971 | 3/1993 | Bonutti | 606/192 |
| 5,242,437 | * 9/1993 | Everett et al. | 606/15 |
| 5,246,421 | 9/1993 | Saab | 604/96 |
| 5,256,139 | 10/1993 | Ghodsian | 604/49 |
| 5,269,753 | 12/1993 | Wilk | 604/49 |
| 5,273,026 | 12/1993 | Wilk | 128/20 |
| 5,275,610 | 1/1994 | Eberbach | 606/198 |
| 5,295,952 | 3/1994 | Pietrafitta | 604/1 |
| 5,300,085 | 4/1994 | Yock | 606/191 |
| 5,301,682 | 4/1994 | Debbas | 128/737 |
| 5,308,327 | 5/1994 | Heaven | 604/96 |
| 5,309,896 | 5/1994 | Moll | 128/20 |
| 5,318,586 | 6/1994 | Ereren | 606/192 |
| 5,320,604 | 6/1994 | Walker | 604/96 |
| 5,320,605 | 6/1994 | Sahota | 604/101 |
| 5,331,947 | 7/1994 | Shturman | 126/4 |
| 5,345,927 | 9/1994 | Bonutti | 128/20 |
| 5,354,270 | 10/1994 | Wilk | 604/500 |
| 5,359,995 | 11/1994 | Sewell, Jr. | 128/20 |
| 5,364,356 | 11/1994 | Hofling | 604/96 |
| 5,400,770 | 3/1995 | Nakao | 128/4 |
| 5,405,360 | 4/1995 | Tovey | 606/151 |
| 5,649,902 | * 7/1997 | Yoon | 604/1 |

OTHER PUBLICATIONS

New Directions in Laparoscopy, Origin, Product Specification Sheet.

Soft–Wand: A Traumatic Tissue Manipulation Balloon, Cabot Medical, Transplantation Trends, 3/94, 22.

Leadership Through Innovation, Advanced Surgical, 3/94, 13.

Expose Retractor: Reusable Retractor, Advanced Surgical, Product Specification Sheet.

A Conservative Approach to Laparoscopic Hernia . . . , Origin, Product Specification Sheet.

* cited by examiner

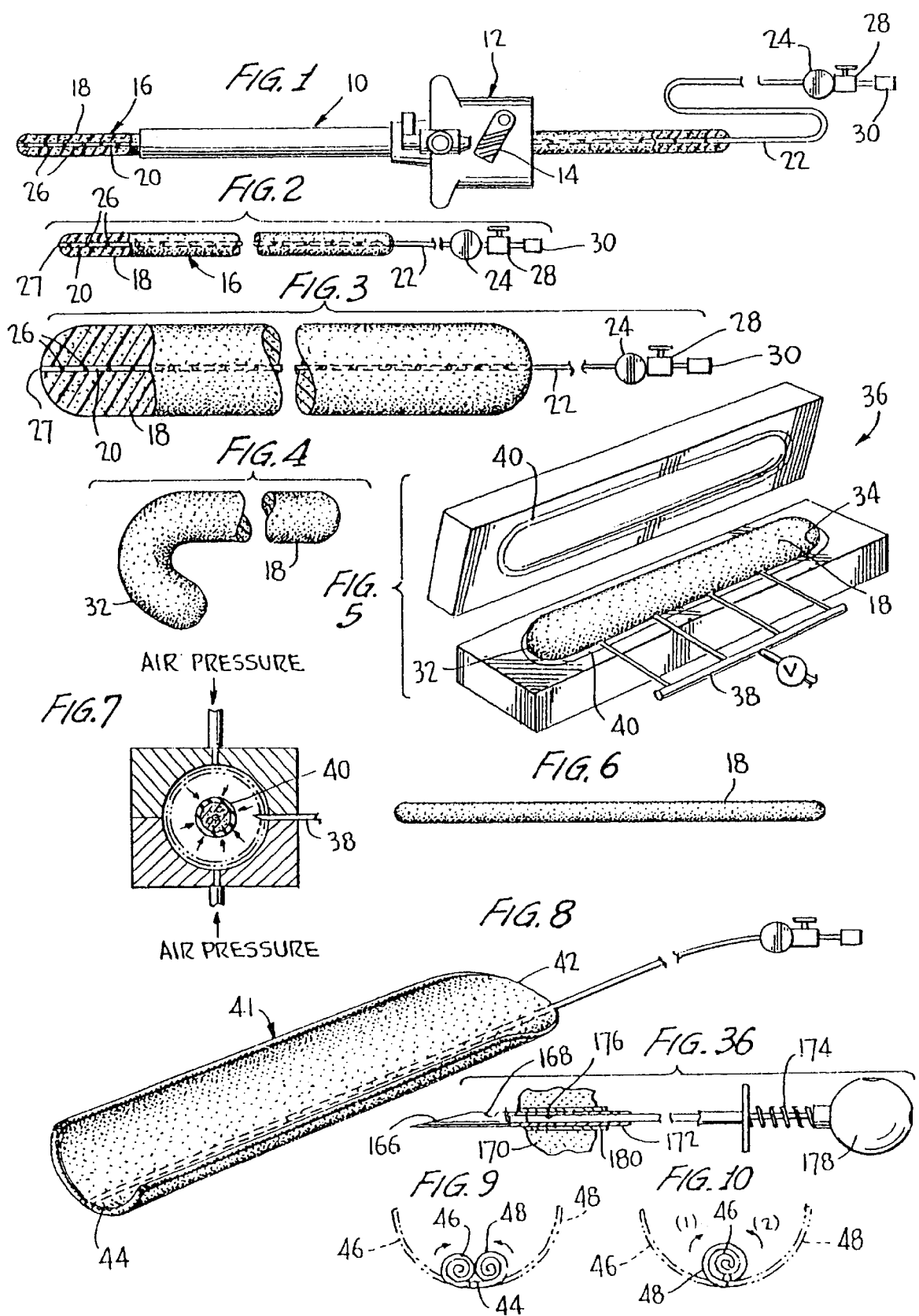

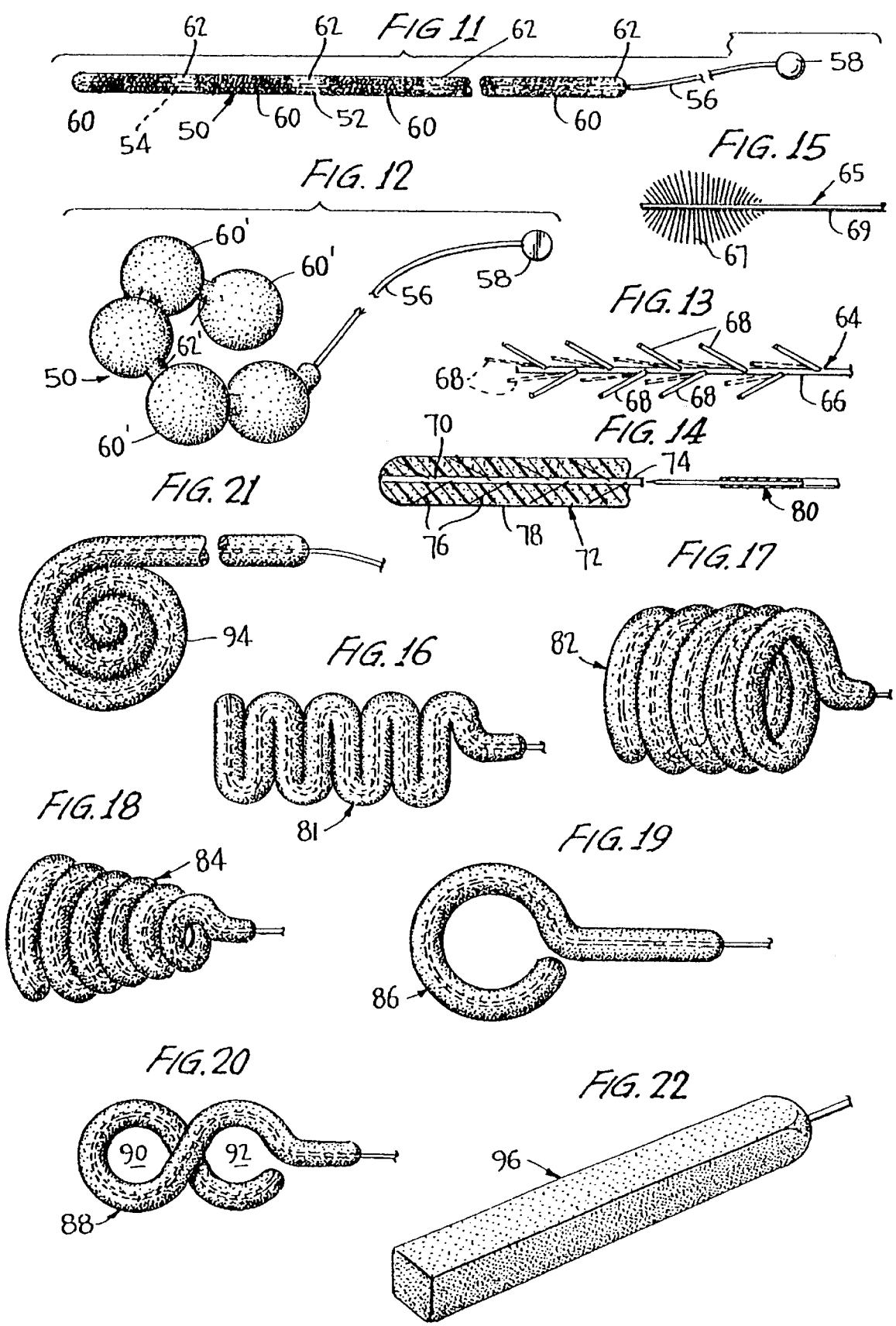

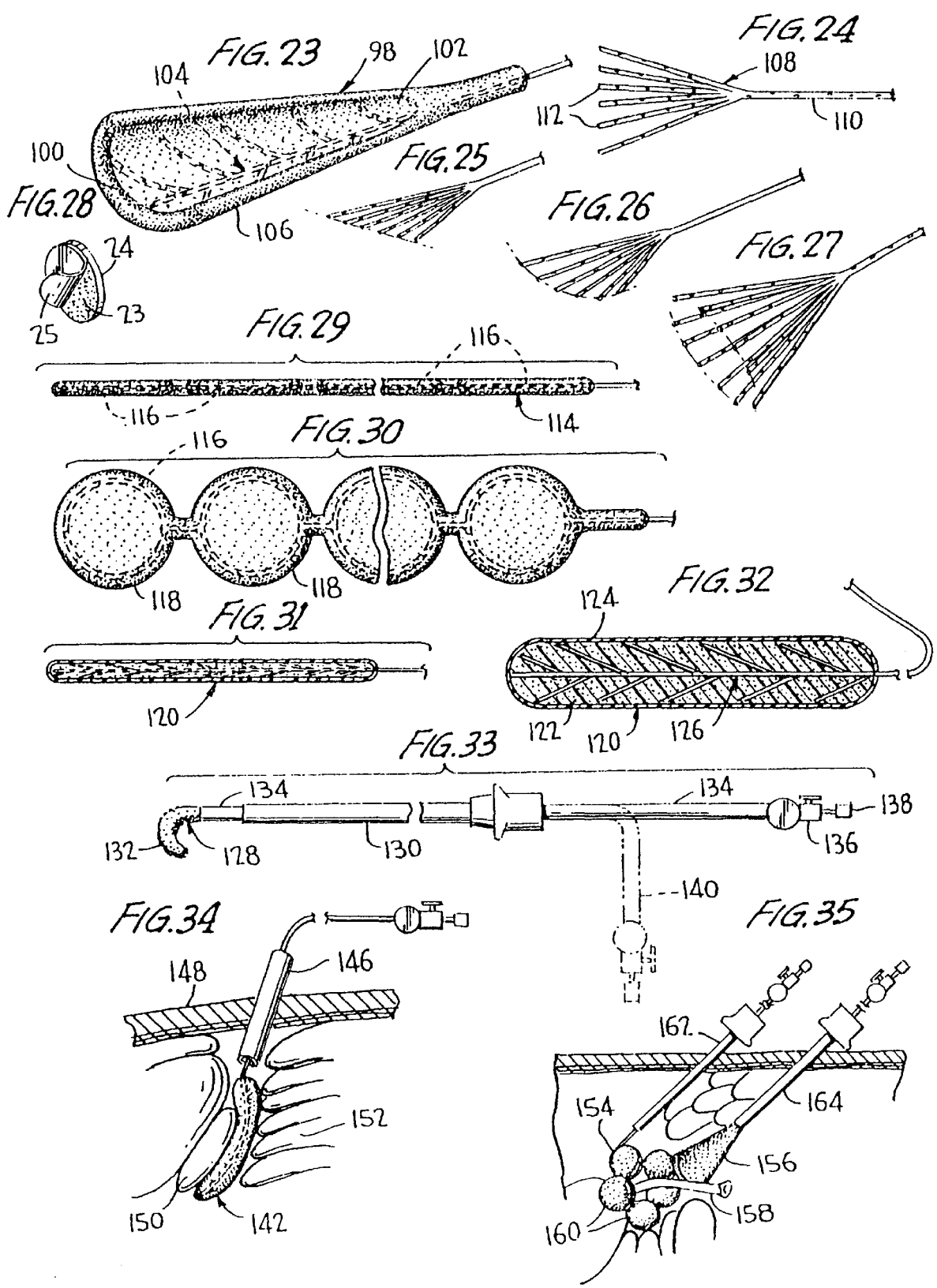

METHOD FOR ABLATING PORTIONS OF THE UTERUS

CROSS-REFERENCE TO RELATED PATENT APPLICATIONS

This application is a continuation of patent application Ser. No. 08/595,461, filed Feb. 5, 1996 now U.S. Pat. No. 5,773,252, which is a continuation of patent application Ser. No. 08/295,022, file Aug. 25, 1994 and now abandoned, which is a division of patent application Ser. No. 08/130,484, filed Oct. 1, 1993 now U.S. Pat. No. 5,484,426, which is a division of patent application Ser. No. 07/600,775, filed Oct. 23, 1990 and now U.S. Pat. No. 5,374,261, which is a continuation-in-part of patent application Ser. No. 07/556,081, filed Jul. 24, 1990 and now U.S. Pat. No. 5,074,840 and this application is also a continuation-in-part of patent application Ser. No. 08/768,239, filed Dec. 17, 1996 now U.S. Pat. No. 5,782,800, which is a continuation of patent application Ser. No. 08/441,465, filed May 15, 1995 and now U.S. Pat. No. 5,656,013, which is a division of patent application Ser. No. 08/249,116, filed May 25, 1994 and now U.S. Pat. No. 5,514,091 which is a continuation-in-part of patent application Ser. No. 07/596,937, filed Oct. 15, 1990 and now abandoned. The disclosures of the above applications are incorporated herein by reference.

BACKGROUND OF THE INVENTION

1. Field of the Invention

The present invention pertains to multifunctional devices for use at an operative site for increased visualization of the operative field, manipulation of tissue, exposure and isolation of tissue, absorption of body fluids and/or treatment of tissue, and, more particularly, to such devices for use in endoscopically performed operative procedures and methods therefor.

2. Discussion of the Prior Art

Endoscopically performed operative procedures are preferred for surgery on the human body due to their least invasive nature and reduced trauma and tissue damage as compared with open surgery. There are many common endoscopically performed operative procedures including, for example, laparoscopy (pelviscopy), gastroentroscopy, laryngobronchoscopy thoracoscopy, arthroscopy and the like. While endoscopically performed operative procedures are preferred, there are obstacles to expanding endoscopy to include the various procedures currently performed with open surgery. One of the obstacles is that packing of the internal operative site has not been able to be accomplished in the past due to the fact that access to the operative site is available only through a narrow portal normally including a cylindrical sleeve positioned by means of a puncturing instrument. Without packing, endoscopic procedures are much more difficult and dangerous to perform, even with the use of insufflation and instruments particularly useful in endoscopy, such as laser and electrosurgical instruments, since the tissue or organ structure cannot be adequately exposed and manipulated, the surrounding tissue and organ structure is not protected during the procedure and body fluids cannot be removed from the operative site without the use of expensive and cumbersome suction equipment. Effective exposure of diagnostic and surgical sites is vitally important in order to carry out successful procedures.

Many presently performed endoscopic procedures are implemented with the use of electrosurgical or laser instruments for coagulation and cutting which presents the opportunity for accidental contact or scarring of tissue not intended to be treated if the operative site is not adequately packed to expose and isolate the tissue to be treated and if vision is impaired by blood or other body fluids. Accordingly, while laser and electrosurgical probes can be introduced through narrow portals to permit various types of procedures to be performed endoscopically, great care is required to assure that adjacent tissue is not inadvertently damaged thus resulting in increased time to complete the surgery. In most endoscopic procedures, there is very little space in which to maneuver instruments; and, in many cases, tissue surrounding the operative site must be retracted or repositioned to facilitate the procedure. During open surgery, sponges or other absorbent materials are used to isolate and expose the operative site, and clear vision can be achieved by absorbing or aspirating body fluids, such as blood or the like, due to the large access area to the operative site. For closed or endoscopic surgery, however, access to the operative site is limited, and facilitating procedures cannot be achieved, such as, for example, cleaning and wiping of the tissue during coagulation and cutting, manipulation of the tissue during coagulation and cutting, lysis of adhesion, and irrigation and/or aspiration for cases where cystic fluid has been released.

Preferably, electric or laser coagulation and cutting is performed with simultaneous manipulation of tissue, cleaning and wiping of tissue, irrigation and/or aspiration, and biopsy and culture procedures; however, these functions could not be provided during endoscopic procedures in the past. Where coagulation of large surfaces is required, such as cystic cavity coagulation or endometrial ablation, endoscopic procedures have the disadvantages of requiring substantial time and increasing the chance for accidental scarring or contact.

There is a great need to expand the types of procedures that can be endoscopically performed in order to decrease trauma and recovery time for patients while simultaneously reducing medical costs. Accordingly, much effort has been expended in the development of endoscopic instruments for specific procedures; however, to date, no adequate system has been devised to permit adequate exposure during endoscopically performed operative procedures. The use of gas and liquid insufflation is presently the only option available to expose diagnostic and surgical sites but is not adequate for many procedures and has disadvantages due to the high pressure in the body which can cause pulmonary problems, such as asymptomatic diaphragmatic hernias.

SUMMARY OF THE INVENTION

Accordingly, it is a primary object of the present invention to provide multifunctional devices for use in endoscopically performed operative procedures to expand the types of procedures that can be performed endoscopically while increasing patient safety and exposure of operative sites in endoscopic procedures presently being performed.

Another object of the present invention is to overcome the above mentioned disadvantages in endoscopic procedures utilizing electric or laser coagulation and cutting by providing the availability of simultaneous tissue manipulation, cleaning and wiping of tissue, irrigation and/or aspiration and vision enhancement.

A further object of the present invention is to increase visualization of operative fields or sites and to expose and isolate operative sites with the use of packing devices having shapes and configurations facilitating positioning of the devices in the body and use with specific organ structures and procedures.

Another object of the present invention is to provide a sponge-like, fluid absorbing device having a substantially rigid dry state allowing passage through a narrow endoscopic portal, such as a trocar sleeve, a cannula, an endoscope operating channel or the like, and permitting tissue manipulation and precise positioning at an internal operative site to expose tissue and organ structures to be treated, absorb body fluids and protect adjacent tissue and organ structures.

A further object of the present invention is to pack an internal operative site through a narrow endoscopic portal, that is a narrow portal for performing procedures with visualization through an endoscope, using a length of absorbent material having a rigid, dry state prior to use and a soft flexible, wet state when exposed to body fluids.

Yet an additional object of the present invention is to endoscopically pack an internal operative site using a length of absorbent material having a relatively straight configuration in a dry state and assuming a non-straight configuration in a wet state to allow the material to have a predetermined configuration when positioned at the operative site to absorb body fluids.

The present invention is generally characterized in a multifunctional device for use in an endoscopically performed operative procedure of the type where a narrow portal is established through the skin to provide access to an operative site and the multifunctional device is introduced to the operative site through the narrow portal. The multifunctional device is formed of an absorbent material, preferably expandable, having a substantially rigid dry state prior to introduction to the operative site and a soft, flexible wet state after absorbing fluids. The absorbent material can be formed with a spine therein of either a continuous or a discontinuous, segmented construction, and the spine can be branched and tubular or solid. The absorbent material can have portions or segments thereof expandable to different sizes to produce rounded protuberances to facilitate manipulation at the operative site and can have predetermined, non-straight configurations in the wet state, the predetermined configurations being controlled by the spine in the absorbent material or the method of forming the absorbent material. The multifunctional device can have a passage therethrough to accommodate laser, electrosurgical, biopsy or culturing instruments. Some of the advantages of the present invention over the prior art are that precise packing at an internal operative site is accomplished via a narrow portal thereby expanding the types of procedures that can be performed endoscopically and, further, increasing safety and efficacy in endoscopic procedures in general, that use of the devices provides improved exposure of the operative site, protects surrounding organ structure, allows cultures to be taken, allows irrigation and/or aspiration or drainage with a cleansing effect to minimize the opportunity for inadvertent or catastrophic complications, that the devices are sufficiently rigid or stiff in a dry state to allow precise placement thereof as well as manipulation of tissue, that the devices facilitate removal of infected fluids, such as pus, and abnormal fluids, such as cystic fluids, that the packing devices serve as a culturing medium to identify specific infected organisms or specific malignant cells, that the devices can be used to apply medicaments to tissue and can contain specific medications for specific purposes, such as antiseptics, antibiotics, chemotherapeutic agents or anti-adhesive agents or radiopaque materials for identification or location purposes, and that, when a plurality of packing devices are used in an endoscopic procedure, each packing device is individually identified externally to confirm the number of packing devices and the location of each packing device.

Other objects and advantages of the present invention will become apparent from the following description of the preferred embodiments taken in conjunction with the accompanying drawings.

BRIEF DESCRIPTION OF THE DRAWINGS

FIG. 1 is a top plan view of a multifunctional device in combination with a trocar sleeve in accordance with the present invention.

FIG. 2 is a broken top plan view of the multifunctional device of FIG. 1 in a dry state.

FIG. 3 is a broken top plan view of the multifunctional device of FIG. 2 in an expanded, wet state.

FIG. 4 is a broken view of a multifunctional device according to the present invention having a hook-shape in an expanded state.

FIGS. 5 and 7 are perspective and sectional views, respectively, illustrating the forming of the multifunctional device shown in FIG. 4 to have a compressed rigid dry state as illustrated in FIG. 6.

FIG. 8 is a perspective view of a multifunctional device according to the present invention having a trough-like configuration.

FIGS. 9 and 10 are end views of the multifunctional device of FIG. 8 illustrating the formation of the configuration in the dry state.

FIG. 11 is a broken view of a multifunctional device according to the present invention in a dry state.

FIG. 12 is a perspective view of the multifunctional device of FIG. 11 in a wet state.

FIG. 13 is a plan view of a branched tubular spine for use in a multifunctional device according to the present invention.

FIG. 14 is a broken sectional view of a multifunctional device according to the present invention having a tubular spine with branches and adapted to receive an electrosurgical or laser probe.

FIG. 15 is a plan view of a spine having branches extending therefrom in a particular configuration to conform to an anatomical cavity or surface.

FIG. 16 is a top plan view of a multifunctional device according to the present invention having a serpentine configuration in the wet state.

FIG. 17 is a perspective view of a multifunctional device according to the present invention having a coiled configuration.

FIG. 18 is a perspective view of a multifunctional device according to the present invention having a helical configuration.

FIG. 19 is a top plan view of a multifunctional device according to the present invention having a circular configuration to produce a lumen therein.

FIG. 20 is a top plan view of a multifunctional device according to the present invention having a figure "8" configuration to form a pair of lumens therein.

FIG. 21 is a top plan view of a multifunctional device according to the present invention having a spiral configuration.

FIG. 22 is a perspective view of a multifunctional device according to the present invention having a square configuration in cross-section.

FIG. 23 is a perspective view of a multifunctional device according to the present invention having a spoon-like configuration.

FIG. 24 is a top plan view of a spine for a multifunctional device according to the present invention having a plurality of branches extending from the distal end thereof.

FIGS. 25, 26 and 27 are perspective view of the spine configuration of FIG. 24 for producing linear, curved and circular configurations, respectively.

FIG. 28 is a perspective view of a tag for use with the multifunctional device according to the present invention.

FIG. 29 is a broken top plan view of a multifunctional device according to the present invention having a spine with closed loop segments.

FIG. 30 is a broken top plan view of the multifunctional device of FIG. 29 in a wet state.

FIG. 31 is a sectional view of a multifunctional device according to the present invention covered by an elastic membrane.

FIG. 32 is a sectional view of the multifunctional device of FIG. 31 in a wet state.

FIG. 33 is a top plan view of a multifunctional device according to the present invention in a trocar sleeve with a bendable manipulator.

FIGS. 34 and 35 are broken views, partly in section, illustrating use of the multifunctional devices of the present invention.

FIG. 36 is a broken view, partly in section, of a multifunctional device according to the present invention utilized with a biopsy instrument.

DESCRIPTION OF THE PREFERRED EMBODIMENTS

A multifunctional device in combination with a trocar sleeve in accordance with the present invention is shown in FIG. 1. The trocar sleeve 10 terminates at its proximal end at a hub 12 having a valve 14 therein forming a passage that can be opened to permit instruments to pass through sleeve 10. The trocar sleeve, hub and valve form a conventional trocar assembly commonly used in laparoscopy wherein a trocar, not shown, passes through sleeve 10 and is used to puncture a pneumoperitoneum and is thereafter withdrawn leaving the sleeve in place to form a portal to gain access to an internal operative site. The term "operative site" as used herein refers to any diagnostic, surgical or treatment site or field in the body. The multifunctional device 16 of the present invention can be used with any type of narrow portal providing access to an internal operative site, with or without a sleeve, a cannula or the operating channel of an endoscope; and, the trocar sleeve 10 is exemplary only. The terms "endoscopic portal" and "narrow portal" as used herein mean any small opening providing access to internal operative sites regardless of whether the opening is formed as a structural channel, such as a sleeve, a cannula or the operating channel of an endoscope, or a narrow incisional or natural entry opening.

The multifunctional device 16 is formed of an elongate length of absorbent, preferably expandable, material 18 having a rod-like, substantially straight configuration in a dry state, as shown in FIG. 2, and a tubular spine 20 is disposed in the material. The material 18 can be any type of medical grade absorbent material that can absorb body fluids and, preferably, expand substantially from its size in a dry state, the expansion being dependent upon the procedure being performed and the size of the endoscopic portal. The material is relatively rigid or stiff in the dry state to allow introduction to the operative site through the portal and its use to manipulate tissue prior to absorption of body fluids; however, some flexibility may be desired dependent upon the configuration of the endoscopic portal and the procedure to be performed. While an expandable material is preferred to facilitate packing and tissue exposure, if desired, the absorbent material can be non-expandable as long as the material becomes soft and pliant in the wet state after absorption of body fluids. That is, the material should have the characteristics, when wet, of being soft enough to bend freely and repeatedly without breaking and of being malleable and flexible. Sponge materials have been found to be the most effective for the device. Examples of materials 18 include compressed cellulose sponge, natural sponge, synthetic sponge made of a reaction product of polyvinyl alcohol and formaldehyde, hydrophilic cross-linked polyurethane foam as disclosed in U.S. Pat. No. 3,369,544 to Crockford, No. 3,903,232 to Wood et al, No. 4,098,728 to Rosenblatt and No. 4,553,966 to Korteweg, and compacted gauze or cotton. In the dry state, the multifunctional device must be sufficiently rigid to allow the device to be manipulated in a fashion to be positioned adjacent an operative site to expose and isolate tissue or organ structure to be visualized and/or treated, the rigid nature of the device 16 also allowing the device to be used to contact and move or position tissue and organ structures to facilitate the procedure to be endoscopically performed. In the dry state, the device is essentially a sponge stick. The length and width or lateral size of the device will depend upon the procedure to be endoscopically performed; and, as shown in FIG. 1, the device has a length longer than the length of the trocar sleeve and hub.

The construction of the device 16 is dependent upon the type of absorbent material employed and the procedure to be performed including the force required to remove the device after the procedure is completed. To this end, the spine 20 can pass centrally through the material 18, as shown, to form a core-like support attached to the material along the length thereof or can extend through or along material 18 at any position, or the material can have no spine. A connector 22 is fixed to the proximal end of material 18 and has sufficient tensile strength to prevent breakage when the device is pulled from the body by grasping the connector or a tag 24 fixed to the end of the connector. The connector can be flexible, rigid and/or bendable, as will be explained hereinafter, and the spine and connector can be integrally made of one-piece and be hollow or solid. When the spine passes through the material, it can be radiopague to enhance visualization thereof, and the material 18 can also be radiopaque and can have medicaments therein. The tag 24 can also be radiopaque and, preferably, carries indicia for identifying each device, the indicia taking the form of different colors and/or alpha-numeric labeling. As shown in FIG. 28, the tag 24 can have an adhesive coating 23 covered by removable release paper 25 to permit the tag to be secured to equipment external of the body.

The device 16 is shown in FIG. 3 after contact with body fluids which are absorbed by material 18 to cause the material to expand and become soft and flexible to facilitate use of the swollen device to pack the operative site. The spine 20 and connector 22, as shown, are made integrally as one piece and are tubular, and spine 20 has lateral holes 26 therein and an open distal end 27. Adjacent tag 24 is a valve or stop cock 28 communicating with connector 22 and having a coupling 30 adapted to communicate with a source of suction or with a source of irrigating fluid for supply to the operative site. The holes or perforations 26 allow selective or continuous drainage of body fluids through spine 20 and connector 22 when the device is wet. Additionally, medicaments or other therapeutic substances can be introduced to the operative site via connector 22, spine 20 and material 18.

The spine 20, whether tubular or solid, can be formed of any suitable material such as string, plastic or metal. In accordance with a particularly advantageous embodiment of the present invention, spine 20 has resilient, spring-like properties and has a normal, non-straight configuration designed for a particular operative procedure. For example, spine 20 can have various simple or complex curved or partially straight shapes in the normal state. To this end, the spine can be made of spring metal to have a predetermined non-straight, normal configuration; and, when the device is manufactured, the spine is straightened and the absorbent material 18 is attached to the spine, for example with adhesive, such that the dry, stiff condition of material 18 maintains the spine in a substantially straight configuration. Accordingly, the device 16 can be inserted in a straight or linear path through the portal; and, once the device is in the body, material 18 will absorb body fluids to become soft and allow the spine to return to its normal configuration producing a predetermined configuration for use in specific procedures. The shape memory of packing device can be accomplished in other suitable manners, some of which are described hereinafter, and spine 20 can be disposed within material 18 or externally along an outer edge of material 18.

Another manner in which device 16 can be manufactured to have shape memory to assume a predetermined configuration when in a wet state is shown in FIGS. 4, 5, 6 and 7. The sponge is initially molded or cut from a cured sheet of sponge material to have a hook-like, distal end configuration 32 as shown in FIG. 4 with a relatively stable shape, and the soft cured sponge is placed in a substantially straight recess 34 in a two-part fixture 36. The sponge 18 is dried by heating and via fluid withdrawn through manifold 38; and, as the sponge shrinks, a bladder 40 is forced against the sponge 18 to maintain a substantially straight configuration. The dried sponge will, thus, have the shape shown in FIG. 6 and will retain this rod or stick-like shape in the dry state. In use, when the device is introduced into the body via a portal, the sponge 18 will absorb body fluids and, when wet, will return to the expanded hook-like shape shown in FIG. 4.

A multifunctional device 41 having a trough-like configuration is illustrated in FIG. 8, the device having a tapered proximal and 42 and tubular spine 44 running centrally therethrough with lateral and end holes therein as described above with respect to spine 20. The configuration illustrated in FIG. 8 is assumed once the device 41 has been introduced into the body at the operative site, and the configuration of device 41 makes it particularly useful in supporting tubular organ structures in the trough-like recess. In order for the device 41 to have a configuration in a dry state to be introduced through a narrow portal, the portions or wings 46 and 48 on opposite sides of spine 44 can be rolled up to produce longitudinally abutting spiral configurations as illustrated in FIG. 9 where the wings 46 and 48 are shown in their wet or expanded state in phantom. Another manner in which the device 41 can be configured in its dry state is to roll up wing 46 initially as illustrated at (1) in FIG. 10, and thereafter, wind wing 48 around rolled up wing 46 as illustrated at (2). In use, the multifunctional device 41 in the dry state configuration of either FIG. 9 or 10 is introduced through the portal to the operative site; and, once the sponge material of the device absorbs body fluids, the wings 46 and 48 will unroll or unwind to produce the configuration illustrated in FIG. 8 thereby allowing the device 41 to be rigid and manipulate organ structure while the device is being properly positioned and thereafter to unfurl to provide an enveloping packing for the organ structure. By predetermining the size and curvature of the multifunctional device 41, the configuration of the device can be particularly designed to cup a tubular organ structure in the body, such as a bowel, an appendix or a fallopian tube. The device 41 is shown in FIG. 8 using a non-expanding material 18; however, an expanding material can be used if desired.

Another multifunctional device 50 according to the present invention is illustrated in FIG. 11 in its dry state and is formed of a sponge material 52 with a solid spine 54 extending therethrough and continuing from the proximal end to form a connector 56 terminating at a spherical end member 58. The spine and connector can be flexible or semi-flexible or bendable such that positioning of connector 56 either with a bend or by securing end member 58 to equipment external of the body allows positioning of the multifunctional device 50 to be fixed. The sponge material 52 is formed of alternating segments 60 and 62 with segments 60 having a cell or pore density substantially greater than the cell or pore density of segments 62. In this manner, when the device 50 is in the wet state after introduction into the body as illustrated in FIG. 12, the device 50 will have a plurality of protuberant segments to facilitate handling within the body and proper positioning of the device 50 at the operative site. By gradually varying the density of the cells or pores within segments 60, spherical protuberances 60' can be formed in the wet state with the protuberances 60' interconnected by smaller rod-like segments 62' corresponding to segment 62 shown in FIG. 11, segments 62 not expanding to the same size as segments 60 due to the reduced cell or pore density thereof. If it is desired for the multifunctional device 50 to have a general overall configuration, such as circular or hook-shaped, the spine 54 can be a continuous member provided with such configuration in its normal state or, curved spine segments can be disposed at spaced positions in the sponge material only at particular areas, such as in the lower density segments 62, to provide a discontinuous spine. In this manner, the protuberances 60' formed in the wet state will have no spine therein while the connecting segments 62' will have a spine segment therein controlling the overall configuration of the device 50 in the wet state. A circular shape for the overall configuration of the multifunctional device is particularly advantageous for use in surrounding tissue to be treated, such as, for example, the ovary, the fallopian tube or the appendix.

A modification of a spine for use in the multifunctional devices according to the present invention is illustrated in FIG. 13 wherein the spine 64 is formed of a tubular trunk 66 with tubular branches 68 extending therefrom at an acute angle to the distal direction with the branches being flexibly or movably mounted to allow the branches to be compressed to be in substantial alignment with the trunk, as indicated in phantom, when the multifunctional device is in a dry state and the sponge material, not shown, is compressed around the spine and to allow the branches to move outwardly when the device is in the wet state. The branched spine 64 can be either tubular or solid or the branches 68 can be solid with only the trunk 66 tubular. Additionally, the spine can have a normal, non-straight configuration, as discussed above, such that when the device is in a wet state the device will assume a predetermined, non-straight configuration. Additionally, the predetermined configuration can be determined by forming the sponge material in the manner described above with respect to FIGS. 4 through 7.

A branch spine 70 is illustrated in a multifunctional device 72 according to the present invention in FIG. 14 and includes a tubular electrically conductive trunk 74 with electrically conductive solid branches 76 extending angularly therefrom and terminating at tips at the peripheral surface of sponge material 78 when in the wet state. With the embodiment of FIG. 14, an electrosurgical probe 80 can be passed through the portal and through the tubular trunk 74 such that a unipolar electrosurgical device is produced with multiple electrodes defined at the peripheral surface of the sponge. The multifunctional device 72 can, therefore, be efficiently utilized to coagulate large surface areas such as cystic cavities or the endometrium of the uterus. The sponge material 78 will be formed with a specific configuration to conform to the cavity wall to be cauterized thereby substantially decreasing the time required for endometrial ablation, for example, while also assuring complete tissue contact and ablation. A spine 65 is shown in FIG. 15 having branches 67 extending from a trunk 69 in a particular arrangement for use with a sponge material configured to mate with an anatomical cavity.

FIGS. 16 through 21 show various multifunctional configurations particularly advantageous for use with specific procedures at the operative site. The multifunctional device 81 illustrated in FIG. 16 has a serpentine configuration to produce a zig-zag shape changing gradually from the distal end to the proximal end and is particularly useful for abscess drainage. The coiled configuration shown in multifunctional device 82 in FIG. 17 is self-coiling which allows the device 82 to coil around tissue and lift or otherwise manipulate the tissue to position the tissue in the most advantageous position for treatment. The coiled device 82 is particularly useful in procedures requiring packing or manipulation of the ovary, the gall bladder or the appendix, and the soft nature of the sponge material in the wet state produces gentle positioning of the tissue requiring no contact of the tissue with rigid positioning instruments. The increasing diameter coiled spiral configuration of the multifunctional device 84 illustrated in FIG. 18 is particularly advantageous for insertion within an organ, such as the ovary or the fimbrial end, to absorb and/or aspirate body fluid therefrom without leakage into the body cavity. The circular shape of the multifunctional device 86 illustrated in FIG. 19 is particularly advantageous due to the lumen therein for encircling or surrounding tissue such as the ovary, the fallopian tube or the appendix. The double-lumen configuration of the multifunctional device 88 illustrated in FIG. 20 is particularly useful for positioning organ structures adjacent one another to facilitate a procedure. As illustrated, the device 88 has a figure "8" shape in the wet state to define lumens 90 and 92 therethrough for surrounding the organ structures. For example, lumen 90 can be utilized to surround an ovarian follicle while lumen 92 can surround the fimbrial end to position the fimbrial end and the ovarian follicle side-by-side. The spiral, single plane configuration of multifunctional device 94 illustrated in FIG. 21 produces a pad or mat-like large surface area which can be flat or slightly concave and is particularly useful to hold the ovary and collect body fluid during ovarian fluid aspiration with the bowl-shaped embodiment collecting the fluid to assure complete aspiration. All of the configurations discussed above will have a substantially straight, rod-like configuration in the dry state and the predetermined configurations in the wet state can be produced in any desirable manner for example by utilizing spines having such configurations in their normal shape or by forming the devices in the manner discussed above with respect to FIGS. 4 through 7.

A multifunctional device 96 is illustrated in FIG. 22 as having a substantially square or rectangular shape in cross-section and is exemplary of various cross-sectional configurations that can be utilized with multifunctional devices according to the present invention when the devices are in the wet state. It is preferred that, in the dry state, the devices have smoothly curved surfaces such as that provided by a cylindrical or rod-like configuration.

A multifunctional device 98 is illustrated in FIG. 23 having a spoon-like configuration in that the device 98 has a recessed shape in the wet state with a wide curved mouth 100 tapering to a more narrow proximal portion. A branched spine 104 is disposed within the sponge material 106 and is preferably tubular to facilitate aspiration and/or irrigation due to the primary use of device 98 for cupping and lifting organ structures in a soft manner.

When the multifunctional devices are used primarily for tissue manipulation rather than packing, the devices can advantageously include a spine 108 as illustrated in FIG. 24 having a trunk 110 terminating at its distal end at a plurality of angularly extending branches 112. The spine 108 is shown as being entirely tubular; however, it will be appreciated that the spine can have any completely tubular, solid or partly tubular configuration. The arrangement of the branches 112 when the sponge material, not shown, surrounding the spine is in a wet state can have any desired configuration. For example, the branches 112 can be aligned in a straight line as shown in FIG. 25, can be arranged to form a curved or concave alignment as shown in FIG. 26 or can have a circular arrangement as shown in FIG. 27. The fan-shaped arrangement of branches 112 allows the multifunctional devices to be configured as particularly desired to gently engage tissue and organ structure to properly manipulate and position the tissue and organ structure for a particular procedure.

In a multifunctional device 114 shown in FIG. 29, the spine is formed of segments of closed loops 116 with the loop compressed when the sponge material is in the dry state. When the device 114 is in the wet state, as illustrated in FIG. 30, the segments 116 return to their normal configuration to define the shape of the protuberances 118 on the device. The loops 116 are shown as being circular in FIG. 30; however, the loops can have any desired closed configuration, such as triangular, rectangular or polygonal.

In the multifunctional device 120 illustrated in FIGS. 31 and 32 in the dry and wet states, respectively, the sponge material 122 is surrounded by an elastic, stretchable membrane 124, such as silicone rubber, and the spine 126 has a branched configuration with a tubular trunk and tubular branches as previously described with respect to FIG. 13. With the use of the membrane 124, the device 120 can utilize a non-medically accepted sponge material 122, and the expansion of the sponge once introduced into the body through the portal can be achieved by forcing a high viscosity, medical grade, non-toxic fluid, such as 32% dextrose, from a source through the tubular connector and spine to cause the sponge material to expand.

FIG. 33 illustrates a multifunctional device 128 according to the present invention particularly designed for manipulating and positioning tissue and organ structures within the body, the device 128 passing through a trocar sleeve 130. The multifunctional device 128 has a hook or half-circle configuration at its distal end formed of a sponge material 132 with a tubular spine therein, not shown. A tubular, substantially rigid manipulator 134 has a distal end fixed to the proximal end of the sponge material 132 and terminates at its proximal end adjacent a stop cock 136. If a spine is utilized in the sponge material 132, it can extend concentrically within manipulator 134 to communicate with the valve cock 136 and a coupling 138. Since the multifunctional device 128 is particularly designed for manipulating tissue, the manipulator 134 is preferably bendable such that, after introduction into the body via a portal, the sponge material 132 can be utilized to engage tissue or organ structure after assuming its wet curved configuration. Once the tissue or organ structure is engaged with the hook-shaped end of the device 128, the manipulator 134 can be retracted through the sleeve 130 to position or retract the engaged tissue or organ structure. Once the tissue or organ structure is precisely positioned, the manipulator 134 is bent as illustrated at 140 in phantom to engage equipment external of the body and prevent the device 128 from moving internally. Accordingly, manipulator 134 provides the functions of moving the distal end of the device as required to engage and position tissue and also holding the distal end of the device and the engaged tissue in a selected position.

Use of a multifunctional device 142 in accordance with the present invention is illustrated in FIG. 34 wherein the device has been passed through a sleeve 146 that extends through the skin and muscle of the abdomen 148, and the device 142 is positioned between the gall bladder 150 and the bowel 152. The device 142 will preferably have an elongated, spoon-like configuration in the wet state to cup and support the gall bladder for use in performing a cholecystectomy.

Use of multifunctional devices 154 and 156 according to the present invention is illustrated in FIG. 35 to isolate and expose the fallopian tube 158. Device 154 has protuberances 160 and is structured to form a circle to surround and support the fallopian tube 158 which extends through the lumen formed thereby. The device 156 has a spoon-like configuration similar to device 98 shown in FIG. 23 and is utilized to manipulate and position the fallopian tube. The devices 154 and 156 are illustrated passing through separate trocar sleeves 162 and 164, respectively.

By forming the multifunctional devices according to the present invention with a tubular spine, the devices are particularly useful for introducing tissue treating probes such as electrosurgical, laser, biopsy and culturing instruments, in that the sponge material protects the probes from inadvertent contact with tissue other than that intended to be treated as well as providing cleaning, wiping and fluid absorbtion functions. The tubular spine is shown with passage of a biopsy needle therethrough in FIG. 36. The biopsy needle has a sharp distal end 166 adjacent a lateral opening 168; and, due to the use of sponge material 170, the device can be positioned immediately adjacent tissue to be sampled. Movement of an inner member 172 against the bias of a spring 174 allows an opening 176 in the inner member to be aligned with lateral opening 168 to permit communication with a squeeze bulb 178 to collect a biopsy specimen. A laser or electrosurgical probe can similarly be passed through the tubular spine 180 to allow protected use thereof.

From the above, it should be appreciated that endoscopic procedures performed in accordance with the present invention are substantially improved with the multifunctional devices described above. By combining the various features of the multifunctional devices described above, devices can be designed for specific operative procedures to be performed and to provide specific functions for use with instruments used in the procedure. For example, the configurations of the devices in the wet state can be controlled or predetermined, or the devices can remain flexible along the full length thereof. The flexibility or rigidity of the devices in the wet state can be controlled by varying cell or pore density when the sponge material is compressed with rigidity increasing with increasing cell or pore density. In this manner, the rigidity or flexibility of a device can be constant or can vary at portions along the device to facilitate positioning of the device between, around or under tissue. The spine can be rigid or flexible, solid, such as a rod or string, or tubular, continuous or discontinuous (i.e., interrupted or segmented) dependent upon intended use of a device. The use of a tubular spine defines a longitudinal passage through the device to receive various instruments such as electrosurgical and laser probes, endoscopes and aspirating and biopsy needles. The sponge material surrounding the distal portion of the instrument allows simultaneous manipulation of tissue, cleaning and wiping of tissue, and aspiration and/or irrigation at the operative site to increase visualization and facilitate precise positioning and use of the instrument. By providing a conductive path from the tubular trunk to the distal tips of conductive branches extending from the trunk and positioning the distal tips at the peripheral surface of the sponge, electrosurgical coagulation of large sources, such as in cystic cavities, ovarian cystic cavities, endometrium of uterine cavity or other pathological or non-pathological surfaces, can be accomplished simultaneously with a single device in a safe protected environment. To this end, the sponge and branches are configured to mate with the surface or cavity, and portions of the trunk are insulated to control the flow of electricity. The connector extending from the sponge and through the portal can be tubular or solid and flexible, rigid or bendable dependent upon use for the sponge. When the device is primarily used to manipulate tissue, the connector will normally be rigid and, preferably, bendable to fix the device in a retracted position; and, by using geometrical shapes for the proximal end member, the end member can be secured to equipment to fix the device in a retracted position. The tags on the proximal end can be used for identification and can be adhesively secured to equipment or surgical drapes. The devices can have recesses or cavities in the distal ends or the sides of the sponges, and a conical shape for the sponge can be achieved by gradually varying the cell or pore density of the sponge.

Use of the multifunctional devices of the present invention in endoscopic operative procedures, and in many cases in open procedures, allow increased visualization of the operative site, exposure and isolation of the operative site to protect surrounding tissue, manipulation and retraction or positioning of tissue, separation of adhering tissue (lysis of adhesion), obtaining cultures with a soft material so as not to damage tissue, absorbtion and aspiration of body fluids, and introduction of medicaments such as antiseptics, anticoagulants, antiadhesive agents, antichemotherapeutic agents and culture media for aerobic and anaerobic organisms by impregnating the medicaments in the sponge to leak out during the procedure or delivering the medicaments to the sponge via the tubular spine and connector.

Inasmuch as the present invention is subject to many modifications, variations and changes in detail, it is intended that all subject matter discussed above or shown in the illustrative drawings be interpreted as illustrative only and not to be taken in a limiting sense.

What is claimed is:

1. A method of ablating portions of a uterus, comprising the steps of:

inserting a sponge body into the uterus while the sponge body is in a compacted state;

expanding the sponge body to an expanded state after said inserting step; and transferring energy between portions of the uterus and the sponge body with an ablation mechanism.

2. A method as recited in claim 1, wherein said expanding step comprises allowing the sponge body to absorb natural body fluids.

3. A method as recited in claim 1, wherein the ablation mechanism is disposed in the sponge body.

4. A method as recited in claim 1, wherein the ablation mechanism is disposed adjacent to an outer surface of the sponge body.

5. A method as recited in claim 1, wherein said transferring step comprises transferring heat generated by an electrosurgical instrument.

6. A method of ablating portions of a uterus, comprising the steps of:

inserting a moisture permeable member into the uterus;

expanding the moisture permeable member into an expanded state within the uterus to define a peripheral surface of the moisture permeable member in its expanded state; and transferring energy between portions of the uterus and the moisture permeable member with an ablation mechanism.

7. A method as recited in claim 6, further comprising the step of allowing the moisture permeable member to absorb moisture.

8. A method as recited in claim 6, wherein the ablation mechanism is disposed adjacent to the peripheral surface of the moisture permeable member.

9. A method as recited in claim 6, wherein said transferring step comprises transferring heat generated by an electrode.

10. A method as recited in claim 6, wherein the ablation mechanism is a plurality of electrical conductors.

11. A method as recited in claim 6, wherein the moisture permeable member is a sponge.

12. A method as recited in claim 6, wherein the moisture permeable member is dry and rigid when it is inserted into the uterus and wet and flexible in the expanded state.

13. A method as recited in claim 6, wherein the moisture permeable member comprises a electrically conductive trunk.

14. A method as recited in claim 13, wherein the moisture permeable member comprises electrical conductors extending from the trunk.

15. A method of ablating portions of a uterus, comprising the steps of:

inserting a moisture permeable member into the uterus;

expanding the moisture permeable member into an expanded state within the uterus to define a peripheral surface of the moisture permeable member in its expanded state;

transferring heat between portions of the uterus and the moisture permeable member with an electrode disposed adjacent to the peripheral surface of the moisture permeable member; and removing moisture away from the uterus.

16. A method of ablating portions of a body organ, comprising the steps of:

inserting a moisture permeable member into the body organ;

expanding the moisture permeable member into an expanded state within the body organ to define a peripheral surface of the moisture permeable member in its expanded state; and transferring energy between portions of the body organ and the moisture permeable member with an ablation mechanism.

17. A method as recited in claim 16, further comprising the step of allowing the moisture permeable member to absorb moisture.

18. A method as recited in claim 16, wherein the ablation mechanism is disposed adjacent to the peripheral surface of the moisture permeable member.

19. A method as recited in claim 16, wherein the ablation mechanism is disposed at the peripheral surface of the moisture permeable member.

20. A method as recited in claim 16, wherein said transferring step comprises transferring heat generated by an electrode.

21. A method as recited in claim 16, wherein the ablation mechanism is a plurality of electrical conductors.

22. A method as recited in claim 16, wherein the moisture permeable member is a sponge.

23. A method as recited in claim 16, wherein the moisture permeable member is dry and rigid when it is inserted into the body organ and wet and flexible in the expanded state.

24. A method as recited in claim 16, wherein the moisture permeable member comprises a electrically conductive trunk.

25. A method as recited in claim 24, wherein the moisture permeable member comprises electrical conductors extending from the trunk.

* * * * *